US00PP27506P2

(12) United States Plant Patent
van den Hoogen

(10) Patent No.: US PP27,506 P2
(45) Date of Patent: Dec. 27, 2016

(54) ***VERONICA* PLANT NAMED 'ALLLAGUNA'**

(50) Latin Name: ***Veronica longifolia*×*Veronica spicata***
Varietal Denomination: Alllaguna

(71) Applicant: Wilhelmus T. J. van den Hoogen, Cuijk (NL)

(72) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 112 days.

(21) Appl. No.: 14/544,627

(22) Filed: Jan. 28, 2015

(51) Int. Cl.
*A01H 5/02* (2006.01)

(52) U.S. Cl.
USPC ..... Plt./251

(58) Field of Classification Search
USPC ..... Plt./251
See application file for complete search history.

*Primary Examiner* — Susan McCormick Ewoldt
(74) *Attorney, Agent, or Firm* — C. A. Whealy

(57) ABSTRACT

A new and distinct cultivar of *Veronica* plant named 'Alllaguna', characterized by its upright plant habit; freely flowering habit; compact and dense inflorescences with numerous dark blue-colored flowers; and good postproduction longevity.

1 Drawing Sheet

Botanical designation: *Veronica longifolia*×*Veronica spicata*.

Cultivar denomination: 'ALLLAGUNA'.

BACKGROUND OF THE INVENTION

The present invention relates to a new and distinct cultivar of *Veronica* plant, botanically known as *Veronica longifolia*× *Veronica spicata*, typically grown as a cut flower and hereinafter referred to by the name 'Alllaguna'.

The new *Veronica* plant is a naturally-occurring whole plant mutation of *Veronica longifolia*×*Veronica spicata* 'Allbizarre', not patented. The new *Veronica* plant was discovered and selected by the Inventor as a single flowering plant from within a population of plants of 'Allbizarre' grown in a controlled nursery environment in Cuijk, The Netherlands in August, 2012.

Asexual reproduction of the new *Veronica* plant by vegetative cuttings in a controlled environment in Cuijk, The Netherlands, since August, 2012 has shown that the unique features of this new *Veronica* plant are stable and reproduced true to type in successive generations.

SUMMARY OF THE INVENTION

Plants of the new *Veronica* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Alllaguna'. These characteristics in combination distinguish 'Alllaguna' as a new and distinct *Veronica* plant:

1. Upright plant habit.
2. Freely flowering habit.
3. Compact and dense inflorescences with numerous dark blue-colored flowers.
4. Good postproduction longevity.

Plants of the new *Veronica* differ primarily from plants of the parent. 'Allbizarre', in flower color as plants of 'Allbizarre' have pink-colored flowers.

Plants of the new *Veronica* can be compared to plants of *Veronica longifolia* 'Alllove', disclosed in U.S. Plant Pat. No. 21,478. In side-by-side comparisons conducted in Cuijk, The Netherlands, plants of the new *Veronica* differed primarily from plants of 'Alllove' in the flower color as plants of 'Alllove' had red purple-colored flowers.

BRIEF DESCRIPTION OF THE PHOTOGRAPH

The accompanying colored photograph illustrates the overall appearance of the *Veronica* plant showing the colors as true as it is reasonably possible to obtain in colored reproductions of this type. Colors in the photograph may differ slightly from the color values cited in the detailed botanical description which accurately describe the actual colors of the new *Veronica* plant.

The photograph comprises a side perspective view of typical cut flower stems of 'Alllaguna' in a vase.

DETAILED BOTANICAL DESCRIPTION

Plants used for the aforementioned photograph and following description were grown during August in ground beds in an outdoor nursery in Addis Ababa, Ethiopia and under cultural practices typical of commercial *Veronica* production. During the production of the plants, day temperatures ranged from 15° C. to 25° C. and night temperatures ranged from 5° C. to averaged 15° C. Plants were one year old when the photograph and the description were taken. In the following description, color references are made to The Royal Horticultural Society Colour Chart, 2007 Edition, except where general terms of ordinary dictionary significance are used.

Botanical classification: *Veronica longifolia*×*Veronica spicata* 'Alllaguna'.

Parentage: Naturally-occurring whole plant mutation of *Veronica longifolia*×*Veronica spicata* 'Allbizarre', not patented.

Propagation:

*Type cutting*.—Vegetative cuttings.

*Time to initiate roots, summer*.—About 10 to 14 days at temperatures ranging from 12° C. to 30° C.

*Time to produce a rooted young plant, summer*.—About 24 to 32 days at temperatures ranging from 12° C. to 30° C.

*Root description*.—Fine, fleshy; white in color.

*Rooting habit*.—Freely branching; dense.

Plant description:

*Plant type*.—Herbaceous perennial.

*Plant and growth habit*.—Narrow upright inverted triangle; freely basal branching habit with about five flowering stems developing per plant; moderately vigorous to vigorous growth habit.

*Plant height*.—About 71.4 cm.

*Plant width*.—About 28.9 cm.

*Lateral branch description*.—Length: About 63.2 cm. Diameter: About 4.5 mm. Internode length: About 5.3 cm. Strength: Strong. Texture: Sparsely pubescent. Aspect: Erect to about 10° from vertical. Color: Close to 144C.

Leaf description:

*Arrangement*.—Opposite or in whorls of three or four; simple.

*Length*.—About 8.6 cm.

*Width*.—About 3.3 cm.

*Shape*.—Narrowly ovate to broadly lanceolate; slightly to moderately carinate.

*Apex*.—Acute.

*Base*.—Truncate.

*Margin*.—Finely serrate.

*Texture, upper surface*.—Smooth, glabrous.

*Texture, lower surface*.—Moderately pubescent along the main vein.

*Luster, upper surface*.—Slightly glossy.

*Luster, lower surface*.—Matte.

*Venation pattern*.—Pinnate.

*Color*.—Developing leaves, upper surface: Close to 143A. Developing leaves, lower surface: Close to between 144A and 146B. Fully expanded leaves, upper surface: Close to N137B; venation, close to 147B. Fully expanded leaves, lower surface: Close to 147B; venation, close to 147B to 147C.

*Petiole length*.—About 1.7 cm.

*Petiole diameter*.—About 2 mm by 2 mm.

*Petiole texture, upper and lower surfaces*.—Smooth.

*Petiole color, upper surface*.—Close to 146C.

*Petiole color, lower surface*.—Close to 144A to 144B.

Flower description:

*Flower arrangement and shape*.—Single campanulate flowers arranged terminal racemes; racemes compact and dense; racemes typically fasciated; flowers face mostly outwardly.

*Flowering habit*.—Freely flowering habit; about 350 flowers develop per inflorescence.

*Fragrance*.—None detected.

*Natural flowering season*.—Plants begin flowering about eight months after planting; long flowering period, flowering continuous from July to late September in The Netherlands.

*Postproduction longevity*.—Good postproduction longevity; inflorescences maintain good substance for about ten days as a cut flower; flowers not persistent.

*Flower buds*.—Length: About 4.5 mm. Diameter: About 1.5 mm. Shape: Ovoid. Color: Close to 93B.

*Inflorescence height*.—About 9.7 cm.

*Inflorescence diameter*.—About 1.9 cm.

*Flower diameter*.—About 5 mm.

*Flower height*.—About 6 mm.

*Petals*.—Quantity and arrangement: About five in a single whorl, petals fused about 40% of the length from the base. Length: About 6 mm. Width: About 3.5 mm to 4.5 mm. Shape: Obovate. Apex: Obtuse. Margin: Entire. Texture, upper and lower surfaces: Smooth, glabrous. Luster, upper and lower surfaces: Matte. Color: When opening, upper and lower surfaces: Close to N89C. Fully opened, upper and lower surfaces: Close to N89C; color does not fade with development.

*Sepals*.—Quantity and arrangement: About four in a single whorl, sepals fused about 5% of the length from the base. Length: About 2 mm to 3 mm. Width: About 1 mm. Shape: Narrowly ovate. Apex: Acute. Margin: Entire. Texture, upper and lower surfaces: Smooth, glabrous. Luster, upper and lower surfaces: Matte. Color: When opening, upper and lower surfaces: Close to 138C. Fully opened, upper and lower surfaces: Close to 138B.

*Peduncles*.—Length: About 9.5 cm. Diameter: About 4 mm. Aspect: Mostly upright. Strength: Strong. Texture: Smooth, glabrous. Color: Close to 144B.

*Pedicels*.—Length: About 1 mm. Diameter: About 0.5 mm. Aspect: About 45° from peduncle axis. Strength: Strong. Texture: Smooth, glabrous. Color: Close to 144B.

*Reproductive organs*.—Stamens: None observed. Pistils: Quantity per flower: One. Pistil length: About 5.3 mm. Stigma shape: Clavate. Stigma color: Close to 93C. Style length: About 5 mm. Style color: Close to 93C; towards the base, close to N88B. Ovary color: Close to N144D.

*Seeds and fruits*.—Seed and fruit development has not been observed on plants of the new *Veronica*.

Disease & pest resistance: Plants of the new *Veronica* have not been noted to be resistant to pathogens and pests common to *Veronica* plants.

Temperature tolerance: Plants of the new *Veronica* tolerate high temperatures about 35° C. and to be hardy to USDA Hardiness Zone 4.

It is claimed:

1. A new and distinct *Veronica* plant named 'Alllaguna' as illustrated and described.

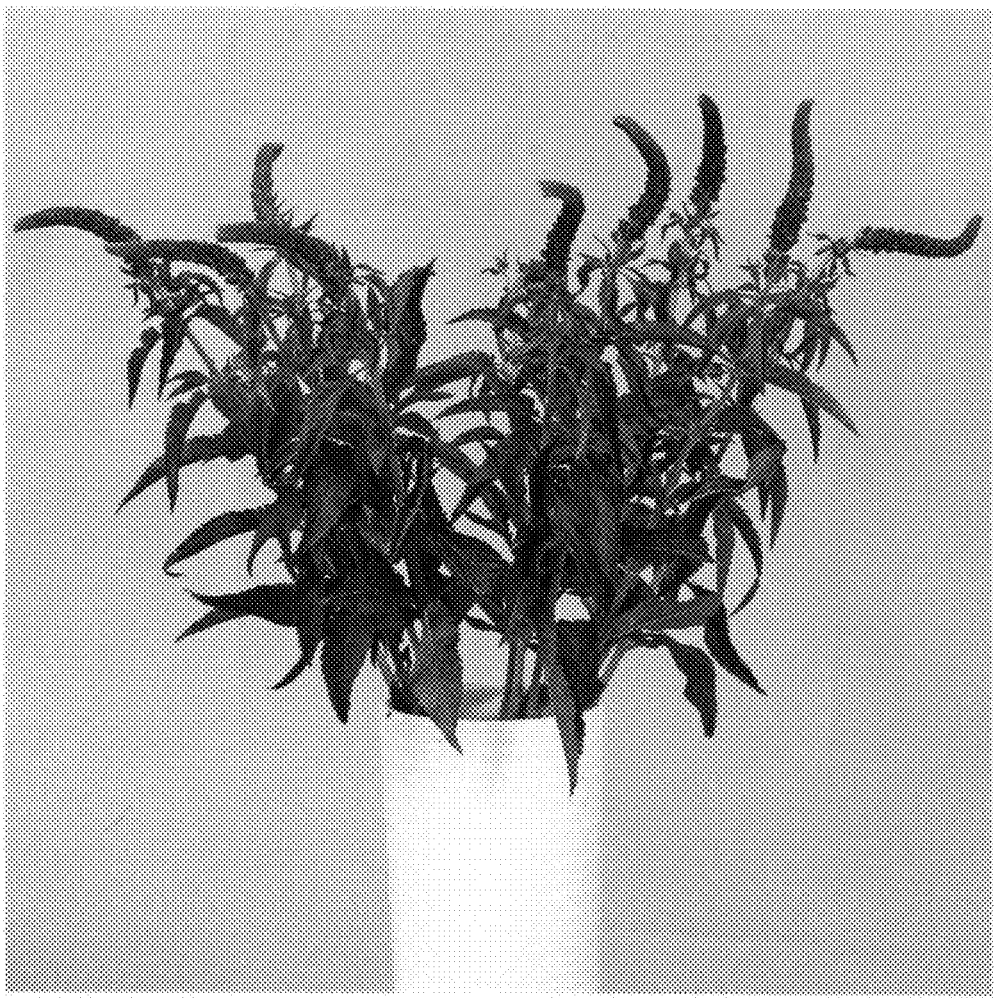

* * * * *